United States Patent [19]

Bailey

[11] Plant 4,832

[45] Mar. 30, 1982

[54] ROSE PLANT

[75] Inventor: Dorothy J. S. Bailey, Bakersfield, Calif.

[73] Assignee: San Joaquin Rose Co., McFarland, Calif.

[21] Appl. No.: 185,241

[22] Filed: Sep. 8, 1980

[51] Int. Cl.[3] ..... A01H 5/00

[52] U.S. Cl. ..... Plt./11

[58] Field of Search ..... Plt./11

*Primary Examiner*—James R. Feyrer

*Attorney, Agent, or Firm*—Vincent G. Gioia

[57] ABSTRACT

A new hybrid tea rose variety of red and cream coloring, long lasting on the plant and as a cut flower.

1 Drawing Figure

1

The present invention relates to a new and distinct variety of rose plant of the hybrid tea rose class, which was originated by my crossing my seedling of (Handel×Granada) as seed parent and the rose known as "Kordes Perfecta" as pollen parent.

Among the novel characteristics possessed by this new variety which distinguish it from its parents and all other varieties of which I am aware are its low growing habit of growth and red and cream colored flowers. Petal undersurface is generally cream colored and petal top surface has pronounced red petal edge. As blooms open, the red color predominates in appearance but cream coloring is much in evidence. Blooms are exceptionally long lasting on the plant and as cut flowers. Asexual reproduction by budding of the new variety as performed in Kern County, Calif., shows that the foregoing and other distinguishing characteristics come true to form and are established and transmitted through succeeding propagations.

The new and improved rose variety which I have developed is a low growing hybrid tea rose with uniquely colored blooms of high centered form displayed on a vigorous spreading, densely foliaged plant with abundant disease resistant foliage. The plants are very floriferous producing lovely floral display throughout the growing season.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "42B" is plate 42B of the Royal Horticultural Society Color Chart.

Parentage: Seedling.

*Seed parent.*—My unpatented, unreleased seedling of (Handel×Granada).

*Pollen parent.*—"Kordes Perfecta".

Class: Hybrid tea.

The following observations are made of specimens grown outdoors in Kern County, Calif. during the months of October and November.

2

FLOWER

Blooming habit: Continuous on short blooming cycles.

A. Bud:

(1) *Size.*—Medium.

(2) *Form.*—Ovoid.

(3) *Color.*—Bicolor buds first reveal pale yellow or cream colored petal undersurface (19D or 20D) after sepals fall, becoming more yellowish toward base (point of attachment) of petal. As petals unfurl reddish colored edge of the petal top surface becomes visible.

(4) *Sepals.*—Thin, pointed, extending just to tip of bud.

(5) *Peduncle.*—Length — short, 1 to 2 inches. Aspect — strong, smooth. Strength — erect. Color — near 146B.

Bloom:

(1) *Size.*—Average size when fully expanded — about 4 to 4½ inches.

(2) *Borne.*—Singly and several together; plant is very floriferous.

(3) *Form.*—High centered at first becoming ruffled at maturity.

(4) *Petalage.*—Number of petals under normal conditions — about 48 to 50 plus petalloids.

(5) *Color.*—As flower buds open, the red and yellow bicoloring becomes increasingly evident. The petal undersurfaces remain more constant cream colored but the petals' top surfaces show dramatic contrast between reddish petal edges (178A in bud stage becoming near 42B as blooms open and mature). However, red coloring appears at petal edge portions slightly washing into relatively clearly delineated cream color (near 19D) similar to petal undersurface on a major portion of the petal. Overall color affect of partially and fully opened blooms is red and cream bicolor.

C. Petals:

(1) *Texture.*—Thick, very good substance.

(2) *Appearance.*—Velvety.

(3) *Form.*—Rounded.

(4) *Arrangement.*—Imbricated.

(5) *Petaloids in center.*—Several.

(6) *Persistence.*—Drop off cleanly.

(7) *Fragrance.*—Slight.

(8) *Lasting quality.*—Very long lasting on plant and as cut flower.

REPRODUCTIVE ORGANS

A. Stamens, filaments and anthers:
(1) *Arrangement.*—Regular.
(2) *Color.*—20A.

B. Pollen:
*Color.*—15B, excellent pollen plant.

C. Styles: Even, medium length.

D. Stigmas:
*Color.*—28C.

E. Hips:
*Shape.*—Globular.
*Size.*—Large.
*Color.*—28A.
*Do seeds protrude?*—No.

PLANT

A. Form: Spreading, bushy.

B. Growth: Very vigorous, dense growth to ground, low growing.
*Height attained.*—About 3 to 3⅓ feet, first season.

C. Foliage: Compound 5 to 7 leaflets.
(1) *Size.*—Medium.
(2) *Quantity.*—Abundant.
(3) *Color.*—New foliage: upper side — reddish green 137A with 60B tones. Under side — near 137C with some 60D. Old foliage: upper side — near 137A. Under side — near 137C.
(4) *Shape.*—Oval.

(5) *Texture.*—Upper side is waxy smooth and under side is textured, leaflets thick.
(6) *Edge.*—Serrated.
(7) *Serration.*—Simple.
(8) *Leaf stem.*—Color — near to 137B. Under side — near 137C.
(9) *Stipules.*—Medium, some bearding.
(10) *Resistance to disease.*—Blackspot — excellent. Mildew — excellent. Rust — excellent.

D. Wood:
(1) *New wood.*—Color — near 146B. Bark — smooth.
(2) *Old wood.*—Color — near 137A. Bark — smooth.

E. Thorns:
(1) *Thorns.*—Quantity (main stalk) — few. On laterals from stalk — very few. Form — recurved. Length — large. Color — 137C with reddish cast. Position — regular.
(2) *Prickles.*—Few.

F. Winter hardiness: Robust winter hardy.

I claim:

1. A new and distinct variety of rose plant of the hybrid tea class, substantially as shown and described, characterized particularly by red and cream colored flowers produced on a vigorous, floriferous plant of good substance and long lasting quality on the plant and as cut flowers.

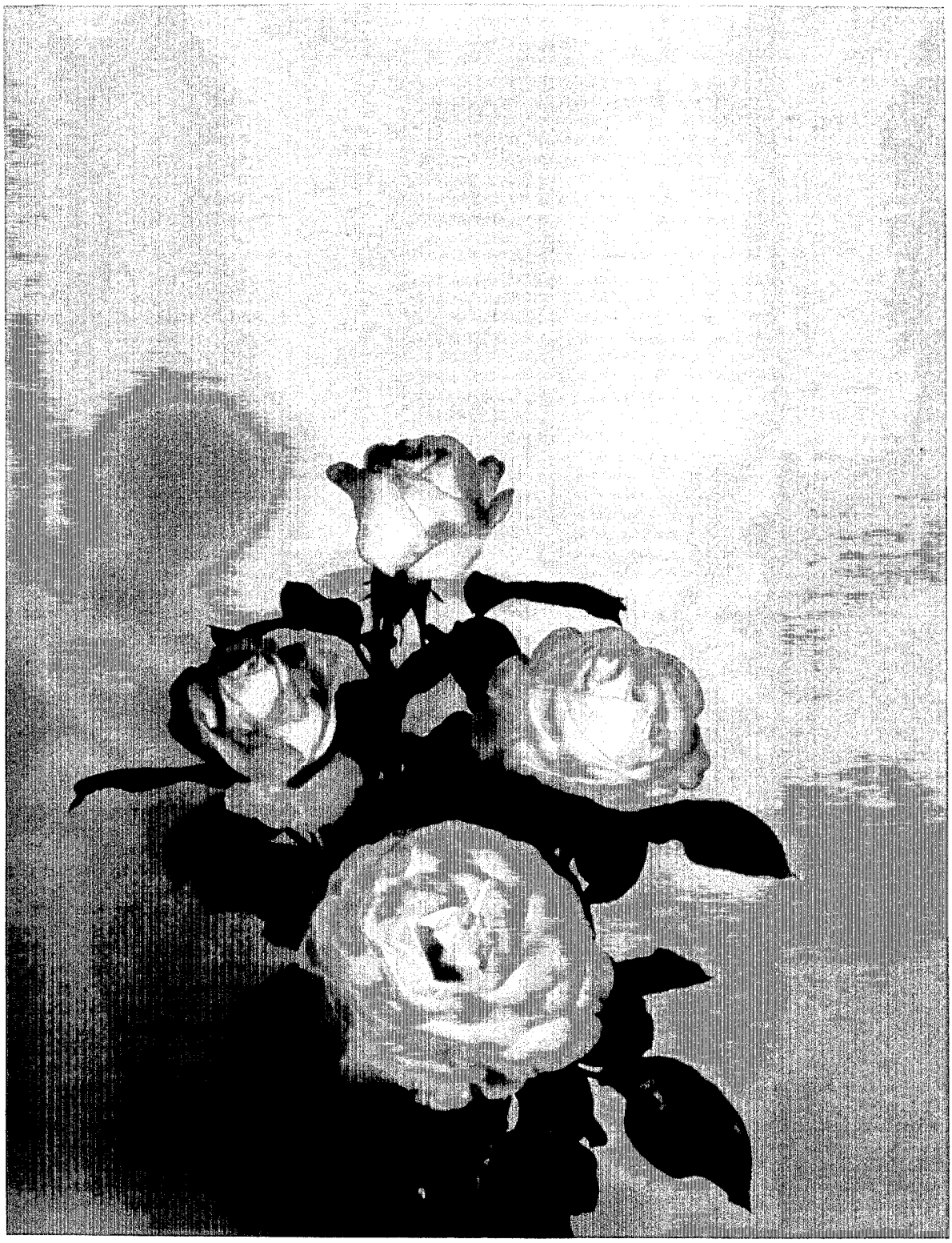

* * * * *